United States Patent [19]

Mattox

[11] Patent Number: 4,954,338
[45] Date of Patent: Sep. 4, 1990

[54] MICROBICIDAL MICROEMULSION
[75] Inventor: John R. Mattox, Perkasie, Pa.
[73] Assignee: Rohm and Haas Company, Philadelphia, Pa.
[21] Appl. No.: 209,620
[22] Filed: Jun. 22, 1988

Related U.S. Application Data

[63] Continuation-in-part of Ser. No. 81,922, Aug. 5, 1987, abandoned.

[51] Int. Cl.$^5$ .................. A61K 31/74; A01N 25/00; A01N 31/14; C11D 3/48
[52] U.S. Cl. .................. 424/78; 424/405; 514/937; 514/723; 106/18.22; 252/106; 523/122
[58] Field of Search .................. 424/78, 405; 252/106; 514/937, 723; 523/122; 106/18.22

[56] References Cited

U.S. PATENT DOCUMENTS

| | | |
|---|---|---|
| 3,683,078 | 8/1972 | Haus . |
| 4,105,431 | 8/1978 | Lewis et al. .................. 252/106 |
| 4,146,499 | 3/1979 | Rosano . |
| 4,567,161 | 1/1986 | Posanski et al. . |
| 4,568,480 | 2/1986 | Thir et al. . |
| 4,618,620 | 12/1986 | Ishigun et al. .................. 514/383 |
| 4,708,720 | 11/1987 | Grangette et al. .................. 44/51 |
| 4,733,677 | 3/1988 | Gee et al. .................. 132/7 |
| 4,783,221 | 11/1988 | Grove .................. 106/18.22 |

FOREIGN PATENT DOCUMENTS

| | | |
|---|---|---|
| 92457 | 1/1983 | European Pat. Off. . |
| 55401 | 3/1983 | European Pat. Off. . |
| 2328192 | 6/1973 | Fed. Rep. of Germany . |
| 3235612 | 9/1982 | Fed. Rep. of Germany . |

OTHER PUBLICATIONS

Microemulsion Theory & Practice, Ed. L. M. Prince, Academic Press (1977), Chapter 6.

Primary Examiner—Merrell C. Cashion, Jr.
Assistant Examiner—Pili Curtis
Attorney, Agent, or Firm—Michael B. Fein

[57] ABSTRACT

Disclosed are dilutable oil-in-water microemulsions of low water soluble microbicidal isothiazolones and their method of preparation.

29 Claims, No Drawings

4,954,338

MICROBICIDAL MICROEMULSION

CROSS REFERENCE

This application is a continuation-in-part of Ser. No. 081,922 which was filed Aug. 5, 1987, now abandoned.

FIELD OF THE INVENTION

Microemulsion of low water soluble isothiazolones which upon dilution with water remain microemulsions. The microemulsions are suitable for use in many applications such as fungicides, slimicides, algaecides, bactericides in any locus.

MICROEMULSIONS

DESCRIPTION OF THE PRIOR ART

Microemulsions are dispersions of one liquid phase in a second immiscible phase. They can be water continuous (o/w) or oil continuous (w/o) where "oil" denotes an organic liquid (or liquids) of low water solubility. A unique property of microemulsions is that the interfacial tension between the two phases is very low, much lower than can be measured with conventional instruments such as a DuNouy Tensiometer. This low interfacial tension results from very specific combinations of "oil" (water immiscible organic liquid) and surfactants and water, and is manifested in the particle size of the dispersed phase being extremely small, usually less than 1000 Å. Since this is small in relation to the wave length of visible light, microemulsions appear opalescent or optically clear. Microemulsions are stable toward phase separation for periods measured in years. This contrasts to the normal macroemulsion, where milky appearance results from emulsion particles being in the 1-20 range, and where phase separation will typically occur within hours to weeks after the emulsion is prepared.

Optimum solubilization of an oil to give an o/w microemulsion can occur within a narrow composition range of oil and surfactant and cosurfactant and water. A typical example is given in *Microemulsion Theory and Practice*, Ed. L. M. Prince, Academic Press (1977) describing the system p-xylene and sodium lauryl sulfate and pentanol and water. When the composition is outside the microemulsion range defined by a phase diagram, multiphase regions exist. The consequence is that dilution of a microemulsion composition with water usually leads to a macroemulsion or multiphase, unstable systems. In a practical sense it is desirable to define a microemulsion composition that will remain clear and not phase separate when further diluted in water.

An o/w micellar solution can result when a small amount of "oil" is added to an aqueous solution of surfactant and water. If the amount of surfactant is great in relation to the "oil" (say >5:1) the oil can migrate to the interior of the surfactant micelle without greatly disturbing it. This solubilizing of the oil can result in a clear micellar solution and will very often retain clarity when further diluted in 30 water. Because of large excesses of surfactant, compositions to give solubilized solutions are not as critical as with microemulsions. A microemulsion represents a much more efficient way of solubilizing an oil.

U.S. Pat. No. 4,567,161 discloses transparent microemulsions with active ingredients (e.g. pesticides, herbicides, pharmaceuticals) together with a phospholipid and a coemulsifier (glycerin ester).

U.S. Pat. No. 4,568,480 discloses preparing microemulsions using alkoxylated phenols where the phenol hydrophobe is a multi-ring system connected by alkylinden groups and the ethoxylated alcohol contains an ester group. These are generally useful with or without any additional phosphate ester alkali metal salt surfactant to prepare microemulsions of cosmetics, toiletries and drugs.

European Patent Application No. 55,401 discloses preparing microemulsions of insecticides and acaricides using an ethoxylated phenol prepared by alkylating tolylethylphenol and phenol with n-methylstyrene.

German Patent No. 32,35,612 AI discloses cold stable aqueous microemulsions of agrochemical pesticides, household pest control agents and pharmaceuticals using an emulsifier which is a mixture of alkylaryl polyglycol and an alkylarylsulfonate salt.

European Patent Application No. 092,457 discloses wood preservation concentrates containing a preservative and insecticides and fungicides formulated with an anionic emulsifier and a coemulsifier such as butoxy ethanol or diethylene glycol monobutyl ether. When further diluted these microemulsions form translucent to opaque dilutions.

U.S. Pat. No. 4,146,499 discloses a method for preparing microemulsions.

Japanese Patent Application No. 52,122-628 discloses oil-in-water microemulsions where insecticides are emulsified with a nonionic surfactant.

European Patent Application No. 160,182 discloses microemulsions of a synthetic pyrethroid insecticide with a sulfonate anionic surfactant and multi-ring phenol ethoxylates.

U.S. Pat. No. 3,683,078 discloses transparent solutions of various pesticides using relatively high levels of various anionic and ethoxylated or propoxylated phenols.

DE No. 2328192 discloses a microemusion of <5% of a water insoluble herbicide with an emulsifier and a hydrotrope.

SUMMARY OF THE INVENTION

This invention describes oil-in-water microemulsions of certain low water soluble isothiazolones which are useful as biocides. By low water soluble is meant the material is soluble in water at less than 1% by weight.

The microemulsions are prepared by combining specifically defined amounts of isothiazolone, anionic surfactants, cosurfactants, polyoxyethylene/polyoxypropylene block copolymers, and water.

Isothiazolones of low water solubility are often prepared as a solution of isothiazolone in a water miscible organic solvent such as propylene glycol. These concentrates are further diluted by the user in water or various aqueous based media to control growth of microorganisms. This approach sometimes has the disadvantage of poor homogeniety of the isothiazolone in the dilution when the solubility of the isothiazolone is exceeded. Often it is desirable to market the isothiazolone at active ingredient levels (AI) of only several percent in the concentrate to be diluted. This requires a large amount of organic solvent per AI unit. A water based concentrate would have substantial cost advantage and environmental advantages by replacing all or most of the organic solvent with water. A microemulsion form of the isothiazolone which would remain a microemulsion upon dilution would overcome these drawbacks. The isothiazolones which may be employed in this invention include those having a water solubility of less than 1% by weight of the formula:

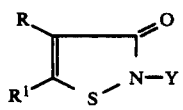

wherein Y is an unsubstituted alkyl group of 2 to 18 carbon atoms,
a substituted alkyl group of 2 to 18 carbon atoms having at least one hydrogen atom replaced by hydroxy, halo, cyano, alkylamino, dialkylamino, phenylamino, halophenylamino, carboxy, carbalkoxy, alkoxy, aryloxy, morpholino, piperidino, pyrrolidonyl, carbamoxy, or isothiazolonyl, wherein the total number of carbon atoms in the substituted alkyl group does not exceed 18,
an unsubstituted or halo-substituted alkenyl group of 4 to 18 carbon atoms,
unsubstituted or halo-substituted alkynyl group of 4 to 18 carbon atoms,
an unsubstituted or alkyl-substituted cycloalkyl group having a four to six carbon atom ring and up to 12 carbon atoms,
an unsubstituted or a halo-, lower alkyl-, or lower alkoxy-substituted aralkyl group wherein the total number of carbon atoms in the aralkyl group does not exceed 10; or
an unsubstituted or a halo-, nitro-, lower alkyl-, or lower carbalkoxy-, substituted aryl group wherein the total number of carbon atoms in the aryl group does not exceed 10; and
R and $R^1$ are the same or different substituent selected from hydrogen, halogen, or a ($C_1$–$C_4$) alkyl group; and One skilled in this art would recognize that the water solubility of the isothiazolones depends on the type of substituent (i.e. R,$R^1$ and Y). For example, the carbon content of the alkyl group will vary depending on the R or $R^1$ or both the R and $R^1$ substituent. As further illustration of what is meant is that, for example, when R=$R^1$=halo, the alkyl group can be as low as two carbon atoms and the water solubility will be less than 1%. When only one of the R or $R^1$ is halo and the other hydrogen, the alkyl group will be at least four carbon atoms. When both R and $R^1$ is hydrogen then the alkyl group must be at least six carbon atoms.

Anionic surfactants which may be employed include alkylaryl sulfonate salts containing from 6 to 20 carbon atoms in the alkyl group such as nonyl benzene sulfonate salts, dodecyl benzene sulfonate salts, tridecylbenzene sulfonate salts and the like; salts of alkyl ($C_8$ to $C_{20}$) sulfates; salts of $C_{10}$ to $C_{20}$ fatty alcohol ethoxylate sulfates containing from 2 to 15 moles of ethylene oxide such as decyl alcohol sulfate salts [$C_{10}H_{23}O(CH_2CH_2O)_2SO_3^-$], dodecyl $EO_{12}$ sulfate salts, and tridecyl $EO_{15}$ sulfate salts; mono or dialkyl ($C_4$ to $C_{13}$) sulfosuccinate salts, such as dioctyl sulfosuccinate salts and ditridecyl sulfosuccinate salts; and sulfated oils such as sulfated castor oil, sulfated neets foot oil and the like.

The counter ion of the sulfonate and sulfate salts described above may be the alkali metal or alkaline earth metal salts such as sodium, potassium, calcium, magnesium, and the like; ammonium salts; mono-, di- or tri-alkyl ammonium salts from amines, such as methyl amine, dimethyl amine, triethyl amine and the like; mono-, di- or tri-hydroxyalkylammonium salts from amines such as ethanol amine, diethanol amine, triethanol amine, and the like. Especially preferred are the sodium salts.

Cosurfactants which can be employed include alkyl alcohols such as ($C_4$–$C_{10}$)alkyl alcohols and, preferably, $C_6$ to $C_8$ alcohols; other cosurfactants include alkyl alkyoxylated alcohols of the formula $CH_3(CH_2)_n(OC_2H_4)_mOH$ or $CH_3(CH_2)_n(OC_3H_6)_mOH$
wherein n is an integer 0 to 7 and preferably 3 to 5 and m is an integer of 1 to 4 and preferably 1 to 2.

The key to this invention is the use of polyoxyethylene and polyoxypropylene block copolymers of the formula:

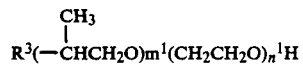

wherein $R^3$ is lower ($C_1$–$C_6$)alkoxy or a radical of the formula $HO(CH_2CH_2O)_{n^1}$—where $m^1$ is an integer greater than 15 and preferably greater than 20 and $n^1$ is an integer greater than 10 and preferably greater than 20 having a molecular weight above 1750 and preferably a molecular weight above 3000 having 10 to 80% by weight of ethylene oxide. This copolymer permits the dilution of the microemulsion which still retains the characteristics of a microemulsion.

In addition, it may be necessary in the use of the microemulsions or in the preparation of the microemulsion, to use various adjuvants including antifoam agents, such as the commerically available silicone antifoam emulsions and the like; antifreeze agents such as propylene glycol, urea and the like; water soluble inorganic salts such as sodium chloride, magnesium sulfate and the like which are used to optimize the action of the surfactant because it increases the concentration of the surfactant at the interface of the microemulsion.

For ease in preparing microemulsions of crystalline isothiazolones, such as 4,5 dichloro-n-octyl isothiazolone, they may be dissolved in water immisicible organic solvents such as aromatic and nonaromatic hydrocarbons, esters, amides, kerosene, dioctylphthalate, dimethyl alkyl ($C_6$–$C_{18}$) amides, xylene, and the like before combining with other ingredients to make the microemulsion.

The range of components is as follows: (All parts by weight percent).

|  | General | Preferred | Most Preferred |
|---|---|---|---|
| Isothiazolone | 0.1–50 | 1–30 | 1–12.5 |
| Anionic Surfactant | 0.1–25 | 1–15 | 1–4 |
| Cosurfactant | 0.1–25 | 1–20 | 1–6 |
| Polyoxyethylene/ polyoxypropylene copolymer | 0.5–50 | 1–40 | 1–10 |
| Water | 10–99 | 20–98 | 50–90 |
| Adjuvants | 0–30 | 0–20 | 0–16 |

The idea of the ratio of total surfactants to emulsified oil is important. The amount of surfactants required to emulsify an oil will depend on the amount of oil in the emulsion, more specifically the interfacial surface area which is proportional to the amount of emulsified oil at a constant particle size. The microemulsions described here have relatively low surfactant to oil ratios, about 1:1. Thus the total surfactant (anionic surfactant and cosurfactant and EO/PO copolymer) required to make a 1% oil emulsion, (1% AI if no solvents are present) is about 1%. Ten percent surfactant would be required to prepare an equivalent 10% AI microemulsion. If the ratio of surfactant to oil becomes great (say >5:1) the compositions are better described as solubilized emulsions or micellar solutions. The compositions required to prepare microemulsions are usually very specific while the exact composition requirements to make a micellar solution are less exacting because of the much greater amount of surfactant used.

These biocidal microemulsions are useful in many areas of preservation including disinfectants, sanitizers, cleaners, deodorizers, liquid and powder soaps, skin removers, oil and grease removers, food processing chemicals, dairy chemicals, food preservatives, animal food preservatives, wood preservation, polymer latices, paint, lazures, stains, mildewcides, hospital and medical antiseptics, medical devices, metal working fluids, cooling water, air washers, petroleum production, paper treatment, pulp and paper slurries, paper mill slimicides, petroleum products, adhesives, textiles, pigment slurries, latexes, leather and hide treatement, petroleum fuel, jet fuel, laundry sanitizers, agricultural formulations, inks, mining, nonwoven fabrics, petroleum storage, rubber, sugar processing, tobacco, swimming pools, photographic rinses, cosmetics, toiletries, pharmaceuticals, chemical toilets, household laundry products, diesel fuel additives, waxes and polishes, oil field applications, and many other applications where water and organic materials come in contact under conditions which allow the growth of undesired microorganisms.

It is well known in the art that the performance of biocides is frequently enhanced by combining with one or more other biocides. In fact, there have been numerous examples of synergistic combinations of biocides. Thus, other known biocides may be combined advantageously with the microemulsions of this invention.

When the concentrate microemulsions (0.1–50% AI) are diluted in water, the microemulsion remains. This is due to the presence of the EO/PO block copolymers. While the use of the anionic surfactant and cosurfactant by themselves at the proper level will form a microemulsion in the concentrate, when diluted, macroemulsions form which phase separate, and sometimes quite rapidly. In contrast, the dilutions described here are stable toward phase separation for months.

Microemulsions, especially those containing nonionic surfactants (EO/PO types here) tend to exhibit phase changes when stored hot or cold. These phase changes are undesirable because ultimately layers may separate. The microemulsions of this invention may be formulated to remain microemulsions at anticipated storage temperatures (0° C. to 54° C.).

The microemulsions of this invention may be formulated to remain microemulsions even when diluted in either soft (e.g. deionized) water or hard (e.g. Army Hard 342 ppm) water.

DETAILED DESCRIPTION

A. Testing Microemulsions (1) The concentrate appearance (a) initial observation at ambient temperature C=clear appearance microemulsion
SO=slightly opalescent microemulsion
=opalescent microemulsion
CL=cloudy appearance macroemulsion P=phase separation—layer(s) formed—unstable macroemulsion (b) observation, hot (54° C.) and cold (0° C.) (same evaluation symbols)

The microemulsion concentrate is prepared and a portion placed in an oven at 54° C. and another portion in a refrigerator at 0° C. An observation is made after temperature equilibration (usually about 2 hours). Another observation is made at a later time (1 to 2 weeks).

(2) Aqueous dilutions

Dilutions are made with 1 part microemulsion and 25 parts water. Initially tap water is used (200 ppm hardness). In later stages a variety of dilutions using water of various hardness levels were evaluated (0, 50, 200, 342 ppm). A rating scale of 0–5 is used to evaluate the clarity of the dilutions. The sample is evaluated immediately after the dilution. Because there can be a tendency for coalescence of emulsified particles with time to give large particles and a corresponding increase in opacity, a second reading is taken at two hours and in the final compositions, at 24 hours. The scale is defined as follows:

0=perfectly clear;
1=clear, very slight opalescence;
2=opalescent;
3=opalescent, slightly cloudy;
4=cloudy (macroemulsion); and
5=phase separation.
(+ is used to denote a slightly lower reading)
(− is used to denote a slightly higher reading)

A rating in the range of 0 to 3 indicate the material is a microemulsion with the rating 3 indicating borderline micro/macro. A rating of 4 indicates a macroemulsion. A rating of 5 indicates unstable macroemulsion with a tendency toward phase separation.

Another rating is the ease with which the microemulsion mixed with water. (Self emulsification SE)
VG=spontaneous mixing, little agitation needed
G=some agitation needed
F=substantial agitation needed The following examples are given by way of illustration only and are not to be considered limiting in any manner.

EXAMPLE 1

Illustrates that dilution of microemulsion forms macroemulsion

Microemulsions could be formed at 12.5% AI by using sodium dodecylbenzenesulfonate as the surfactant and butoxyethanol as the cosurfactant with either the 99% technical or 45% propylene glycol solution of technical isothiazolone.

|  | Experiment A | Experiment B |
|---|---|---|
| n-Octyl-4-isothiazolin-3-one (45%) in propylene glycol[1] | 28.0 | — |
| n-Octyl-4-isothiazolin-3-one (99%) | — | 12.6 |
| (as AI) | (12.6) | (12.5) |
| Sodium dodecylbenzene sulfonate (60% aq) | 10.0 | 10.0 |
| Butoxyethanol | 5.0 | 10.0 |
| Water | 57.0 | 67.4 |
|  | 100.0 | 100.0 |
| Concentrate Appearance | C | C |

-continued

| | Experiment A | Experiment B |
|---|---|---|
| A 1:25 dilution in water of either Experiment A or B resulted in a cloudy macroemulsion which separated on standing. | | |

[1] Subsequently referred to as n-octyl isothiazolone

EXAMPLE 2

Illustrates use of different cosurfactants

| | Wt. % Evaluation of Cosurfactants | | | |
|---|---|---|---|---|
| | A | B | C | D |
| n-Octyl-isothiazolone (45% in propylene glycol) | 28.0 | 28.0 | 28.0 | 28.0 |
| Sodium dodecylbenzene sulfonate (60% aq) | 2.5 | 2.5 | 2.5 | 2.5 |
| $BuPO_{28}EO_{42}OH$ | 5.0 | 5.0 | 5.0 | 5.0 |
| Butoxyethanol | 5.0 | — | — | — |
| n-Hexanol | — | 5.0 | — | — |
| Hexoxyethanol | — | — | 5.0 | — |
| $C_8$–$C_{10}$ Alcohol mixture | — | — | — | 5.0 |
| Water | qs' | qs | qs | qs |
| | 100.0 | 100.0 | 100.0 | 100.0 |
| Concentrate | | | | |
| Initial Appearance Ambient | C | CL | C | C |
| Appearance 24 hr., 54° C. | C | CL | C | SO |
| Appearance 24 hr., 0° C. | C | C | C | C | qs' = quantity sufficient to give 100

Butoxyethanol and hexoxyethanol are preferred cosurfactants. A phase change is seen between ambient temperature and 0° C. with n-hexanol and between ambient temperature and 54° C. with the $C_8$–$C_{10}$ alcohol mixture.

EXAMPLE 3

An experiment to determine the effects of varying three surfactants and the effect of EO/PO on dilution surfactant level. Butoxyethanol has little effect within the range studied.

EXAMPLE 4

Evaluation of Various Hydrophile/-Lipophile Balance Polyoxyethylene/Polyoxypropylene Block Copolymers $R(PO)_m(EO)_nH$

| | $HO(CH_2CH_2O)_n(CHCH_2O)_m(CH_2CH_2O)_nH$ with $CH_3$ branch A-E | | | $BuOPO_mEO_nOH$ F Hydophile-Lipophile |
|---|---|---|---|---|
| Experiment | n | m | mw | Balance (HLB)[1] |
| A | 38 | 54 | 6500 | 15 |
| B | 20 | 54 | 4950 | 9 |
| C | 13 | 30 | 2900 | 15 |
| D | 21 | 67 | 5750 | 8 |
| E | 128 | 54 | 14,600 | 27 |
| F | 29 | 20 | 2,500 | 16 |

The following compositions:

| | #A-F Wt % |
|---|---|
| n-Octylisothiazolone | 12.5 |
| Propylene glycol | 15.5 |
| Sodium dodecyl benzene sulfonate (40% aq) | 4.0 |
| EO/PO surfactant | 6.0 |
| Butoxyethanol | 5.0 |
| Water | 57.0 |
| | 100.0 |

| | A | B | C | D | E | F |
|---|---|---|---|---|---|---|
| Concentrate appearance | C | C | C | C | CL | C |
| 1:25 dilution 2 hr. reading | 2– | 1 | 3 | 1 | 4 | 2 |

[1] HLB is defined - Becher, P; Surfractants in Solution, Vol. 3, Mittal, K. L. and Lindman, B. Eds., Plenum Press, N.Y. 1984, p.925

Conclusion: EO/PO surfactants with an HLB of 8-9 gave the optimum dilution.

| | Wt % | | | | | | | | |
|---|---|---|---|---|---|---|---|---|---|
| | A | B | C | D | E | F | G | H | I |
| n-Octylisothiazolone (45% in propylene glycol) | 28 | 28 | 28 | 28 | 28 | 28 | 28 | 28 | 28 |
| Sodium dodecylbenzene sulfonate (40% aq) | 4 | 6 | 2 | 6 | 2 | 6 | 2 | 6 | 2 |
| $BuPO_{28}EO_{42}OH$ | 5 | 7 | 7 | 3 | 3 | 7 | 7 | 3 | 3 |
| Butoxyethanol | 5 | 7 | 7 | 7 | 7 | 3 | 3 | 3 | 3 |
| Water | 58 | 52 | 56 | 56 | 60 | 56 | 60 | 60 | 64 |
| | 100 | 100 | 100 | 100 | 100 | 100 | 100 | 100 | 100 |
| Concentrate | | | | | | | | | |
| Ambient Temperature Appearance | C | C | C | C | O | C | C | C | O |
| 54° C. Appearance | SO | C | SO | C | O | C | SO | C | O |
| 0° C. Appearance | C | C | C | C | CL | C | C | C | CL |
| Dilution (1:25)[1] | | | | | | | | | |
| Self emulsification (SE) | VG | VG | VG | VG | VG | VG | VG | G | VG |
| Initial appearance | 2 | 1 | 2 | 2 | 3 | 1 | 2 | 2 | 3 |
| 2 hr. appearance | 3 | 2+ | 2– | 3 | 3 | 2 | 2– | 3 | 3 |

[1] Dilution 1 part of concentrate per 25 parts of water

Conclusions: EO/PO surfactant containing formulations 3A through 3I gave transparent microemulsion dilutions unlike Example 1.

The concentrate is clearer with a high sulfonate level at 54°. At 0° the low sulfonate-low EO/PO surfactant gives a cloudy emulsion. The stabilization of the dilution is increased by high sulfonate and high EO/PO

EXAMPLE 5

An Experiment Was Run to Optimize the Microemulsion Containing $HOEO_{21}PO_{67}EO_{21}OH$ Surfactant (These formulations contain a small amount of a 31% silicone emulsions—to eliminate foaming.)

|  | Wt % | | | | | | | | |
|---|---|---|---|---|---|---|---|---|---|
|  | A | B | C | D | E | F | G | H | I |
| n-Octyliso-thiazolone | 12.50 | 12.50 | 12.50 | 12.50 | 12.50 | 12.50 | 12.50 | 12.50 | 12.50 |
| Propylene glycol | 15.50 | 15.50 | 15.50 | 15.50 | 15.50 | 15.50 | 15.50 | 15.50 | 15.50 |
| Dodecylbenzene sulfonate (40% aq) | 6.00 | 6.00 | 4.00 | 4.00 | 6.00 | 6.00 | 4.00 | 4.00 | 5.00 |
| $HOEO_{21}PO_{67}EO_{21}OH$ | 8.00 | 6.00 | 8.00 | 6.00 | 8.00 | 6.00 | 8.00 | 6.00 | 7.00 |
| Butoxyethanol | 6.00 | 6.00 | 6.00 | 6.00 | 4.00 | 4.00 | 4.00 | 4.00 | 5.00 |
| Silicone antifoam emulsion* | 0.01 | 0.01 | 0.01 | 0.01 | 0.01 | 0.01 | 0.01 | 0.01 | 0.01 |
| Water | qs | qs | qs | qs | qs | qs | qs | qs | qs |
|  | 100.00 | 100.00 | 100.00 | 100.00 | 100.00 | 100.00 | 100.00 | 100.00 | 100.00 |
| Concentrate Appearance | | | | | | | | | |
| Ambient Temperature | C | C | C | C | C | C | C | C | C |
| 2 hr. 54° C. | C | C | SO | SO | C | C | SO | SO | C |
| 2 hr. 0° C. | C | C | C | C | C | C | C | C | C |
| 1 hr. 70° C. | C | C | O | O | C | C | SO | O | C |
| 1 hr. 80° C. | C | C | O | O | C | C | SO | O | C |
| 1 hr. 90° C. | C | C | O | O | C | C | SO | O | C |
| 4 days 54° C. | C | C | SO | SO | C | C | SO | C | C |
| 4 days −10° C. | C | C | C | C | C | C | C | C | C |
| Dilution 1:25 | | | | | | | | | |
| SE | VG | VG | VG | VG | VG | VG | VG | VG | VG |
| Appearance | | | | | | | | | |
| Init. 50 ppm hardness | 2 | 3 | 1 | 3 | 2 | 3 | 1 | 3 | 3 |
| 2 hr. 50 ppm hardness | 2 | 4 | 1 | 3 | 2 | 4 | 1 | 3 | 3 |
| Init. 200 ppm hardness | 0 | 1 | 0 | 1− | 0 | 1 | 0 | 1 | 0 |
| 2 hr. 200 ppm hardness | 1 | 1 | 1 | 1 | 1 | 1 | 1 | 1 | 1 |
| Init. 342 ppm hardness | 1 | 1 | 2 | 2 | 1 | 1 | 2 | 1 | 1 |
| 2 hr. 342 ppm hardness | 3 | 3 | 3 | 3+ | 3 | 3 | 3 | 3 | 3 |

*31% aqueous emulsion

The dilution stability of Example 5C and Example G was very good (essentially equivalent) with the formulation of Example 5G having a less noticeable phase change when heated above 54° C. Cold stability at −10° C. is good with all samples.

EXAMPLE 6

An experiment to compare 2 different methods of preparation of the formulation of Example 5C (A) Experiment 5C was repeated by mixing all ingredients except n-octyl isothiazolone and heating the mixture to 50° C. with agitation to form a clear solution. n-Octyl isothiazolone was then added at ambient temperature and a clear microemulsion formed upon agitation.

(B) Experiment 5C was repeated except solution of the $HOEO_{21}PO_{67}EO_{21}OH$ in butoxyethanol was not initially added. A macroemulsion formed when all ingredients except this solution were mixed. When this butoxyethanol solution was added to the macroemulsion a clear microemulsion is formed. The properties of these two microemulsions were evaluated.

|  | 6A | 6B |
|---|---|---|
| Concentrate | | |
| Initial appearance | C | C |
| Appearance 3 days 54° C. | C | C |
| Appearance 3 days 0° C. | C | C |
| Dilution 1:25 | | |
| SE | VG | VG |
| 2 hr. appearance | | |
| 50 ppm hardness | 1 | 1 |
| 200 ppm hardness | 0 | 0 |
| 342 ppm hardness | 2− | 2− |

Conclusion—These two methods of preparation afford equivalent microemulsions.

EXAMPLE 7

Use of 99% Technical n-Octylisothiazolone

|  | Wt % | | | | | | | | |
|---|---|---|---|---|---|---|---|---|---|
|  | A | B | C | D | E | F | G | H | I |
| n-Octyl iso-thiazolone (99%) | 12.60 | 12.60 | 12.60 | 12.60 | 12.60 | 12.60 | 12.60 | 12.60 | 12.60 |
| Sodium dodecylbenzene sulfonate (40% aq) | 5.00 | 5.00 | 5.00 | 5.00 | 3.00 | 3.00 | 3.00 | 3.00 | 4.00 |

-continued

|  | Wt % | | | | | | | | |
|---|---|---|---|---|---|---|---|---|---|
|  | A | B | C | D | E | F | G | H | I |
| $HOEO_{21}PO_{67}EO_{21}OH$ | 9.00 | 7.00 | 7.00 | 9.00 | 9.00 | 9.00 | 7.00 | 7.00 | 8.00 |
| Butoxyethanol | 5.00 | 5.00 | 3.00 | 3.00 | 5.00 | 3.00 | 5.00 | 3.00 | 4.00 |
| Silicone antifoam emulsion | 0.01 | 0.01 | 0.01 | 0.01 | 0.01 | 0.01 | 0.01 | 0.01 | 0.01 |
| Water | qs | qs | qs | qs | qs | qs | qs | qs | qs |
| Concentrate | 100.00 | 100.00 | 100.00 | 100.00 | 100.00 | 100.00 | 100.00 | 100.00 | 100.00 |
| Appearance Ambient Temperature | C | C | C | C | P | CL | CL | CL | CL |
| Appearance 70° C. 2 hr. | C | C | C | C | P | P | P | P | P |
| Appearance 0° C. 2 hr. | C | C | C | C | CL | CL | CL | CL | CL |
| Dilution 1:25 2 hr. reading | | | | | | | | | |
| 0 ppm hardness | 1 | 0 | 2 | 0 | 0 | 0 | 1 | 1 | 1 |
| 200 ppm hardness | 2 | 2 | 1 | 1 | 1 | 1− | 1 | 1− | 2 |

Conclusion: A slightly higher sulfonate level gives a clear concentrate which does not phase separate at hot or cold temperature. The preferred formulation using 99% technical is Example 7D because of dilution stability and lack of concentrate phase changes at 0° C. and 54° C.

EXAMPLE 8

Microemulsion of a Solid Isothiazolone

The solid, 4,5-dichloro-n-octyl-isothiazolone, is dissolved in xylene to form the "oil" to be microemulsified. The following ingredients are mixed together.

|  | Wt % |
|---|---|
| 4,5-dichloro-n-octyl isothiazolone | 10.00 |
| Xylene | 5.00 |
| $C_{12}H_{25}EO_{12}SO_4Na$ + (60% aq) | 8.00 |
| $HOEO_{21}PO_{67}EO_{21}OH$ | 4.00 |
| Butoxyethanol | 25.00 |
| Antifoam | 0.05 |
| 2% aqueous NaCl | 47.95 |
| Total | 100.00 |
| Appearance concentrate | C |
| Appearance dilution (1:25) | 3 |

EXAMPLE 9

Microemulsion of 4,5-Dichloro n-Octyl Isothiazolone

A solution of solid 4,5 dichloro n-octyl isothiazolone in pentyl alcohol was prepared by mild heating. This was added to a mixture of the remaining ingredients and this mixture heated to 50°-60° C. until a clear microemulsion formed.

| Ingredients | Parts by Wt. |
|---|---|
| 4,5 Dichloro n-octyl isothiazolone | 10.00 |
| Pentyl alcohol | 5.00 |
| $HOEO_{21}PO_{67}EO_{21}OH$ | 8.00 |
| $C_{12}H_{25}EO_{12}SO_4Na$ (60% aqueous) | 16.00 |
| Butoxyethanol | 25.00 |
| Antifoam emulsion | 0.05 |
| 2% Aqueous NaCl | 35.95 |
|  | 100.00 |
| Appearance concentrate | C |
| Appearance dilution | 1 |

EXAMPLE 10

Variation of the Cation of Dodecylbenzenesulfonic Acid

10% Aqueous dodecylbenzene sulfonic acid was neutralized with potassium hydroxide, ammonium hydroxide, dimethyl amine and diethanol amine. The following formulation was prepared with each of the 4 DBSA solutions.

| n-Octyl isothiazolone (45% in propylene glycol) | 28.0 |
|---|---|
| 10% DBSA salt solution* | 16.0 |
| Butoxyethanol | 4.0 |
| $HOEO_{21}PO_{67}EO_{21}OH$ | 8.0 |
| Water | 44.0 |
|  | 100.0 |

|  | A | B | C | D |
|---|---|---|---|---|
| DBSA | $K^+$ | $NH_4^+$ | $Me_2NH_2^+$ $NH_2^+$ | $(HOCH_2CH_2)_2$ |
| Concentrate Appearance | | | | |
| Ambient | C | C | C | C |
| Appearance 0° C. | C | C | C | C |
| Appearance 70° C. | C | C | C | C |
| Dilution 24 hr. appearance | | | | |
| 0 ppm | 0− | 0− | 1 | 0− |
| 342 ppm | 0− | 0− | 2 | 0− |

*(the pH of KOH and $NH_4OH$ solution is 7 and the pH of the $(CH_3)_2NH$ and $(HOCH_2CH_2)_2NH$ solution is 6).

Conclusion

All of the above DBSA salts are effective in forming microemulsions. Dimethyl amine is least effective of these four.

EXAMPLE 11

Latex Paints Containing Isothiazolone Microemulsion

Dried exterior latex paint films are susceptible to disfiguring mildew growth. To prevent this an isothiazolone microemulsion is added to the paint A typical exterior latex paint would contain:

|  | parts by wt. |
|---|---|
| Natrosol 250 MHR | 3.0 |

-continued

|  | parts by wt. |
| --- | --- |
| Ethylene glycol | 25.0 |
| Water | 120.0 |
| Tamol ® 960 | 7.1 |
| Potassium tripolyphosphate | 1.5 |
| Triton ® CF-10 | 2.5 |
| Colloid 643 | 1.0 |
| Propylene glycol | 34.0 |
| Ti-Pure R902 (titaniumdioxide) | 225.0 |
| Zinc oxide | 25.0 |
| Minex 4 | 147.3 |
| Icecap K | 50.0 |
| Attagel 50 | 5.0 |

The above materials are ground for 10-15 minutes on Cowles Dissolver at 3800-4500 rpm. The speed is reduced and the following is added:

|  |  |
| --- | --- |
| Rhoplex ® AC 64 | 305.9 |
| Colloid 643 | 3.0 |
| Texanol | 9.3 |
| Microemulsion Example 5C | 7.2 |
| Water | 84.8 |
| 2.5% Natrosol 250 MHR | 118.2 |
|  | 1176.8 |

A 1176.8 batch represents 100 gallons of paint.

The inclusion of the isothiazolone will prevent mildew growth on the paint film under conditions where a paint with on biocide will support mildew growth.

EXAMPLE 12

Use of Isothiazolone Microemulsion in a Water Cooling Tower

Evaporative cooling is widely used for dissipation of heat. This is accomplished with a cooling tower in which a large surface area is exposed by running water down a series of slats. Air is moved over the water surface by fans resulting in evaporation. The cooled water is the heat exchange medium. Fungal growth can occur in the water and on the tower surfaces. This growth can cause several operational problems such as fouling, plugging and wood rot, generally leading to loss of cooling efficiency and biodeterioration of the cooling tower itself. To control fungal growth 5-10 ppm active ingredient of the isothiazolone microemulsion prepared in Example 5G can be added directly to the bulk water in the cooling tower weekly.

EXAMPLE 13

Using Isothiazolone Microemulsions to Prevent Fungal Growth in Metal Working Fluids In the machining of metal parts a metal working fluid is used. This fluid serves to cool, lubricate, and prevent corrosion on the surface being worked. The fluid itself is prepared by adding a metal working concentrate to water. Three gallons Cimcool 5 star 40, a concentrate, is added to 100 gallons of water. This is stored in a sump and pumped to the various machining operations. Spent fluid is returned to the sump for reuse. Over time this fluid can become contaminated with mircoorganism and support fungal growth. This fungal growth can interfere with normal operation by clogging filters in these systems. Addition of 25-50 ppm active ingredient of the isothiazolone microemulsion prepared in Example 4F will control fungal growth.

EXAMPLE 14

Use of Isothiazolone Microemulsion as an Antisapstain Control on Wood

When green lumber is stored in a wet or humid condition, various surface fungal growth can occur which discolors the surface, lowering the value of the lumber. To eliminate this growth an isothiazolone microemulsion is applied to the lumber surface. An aqueous dilution of the microemulsion prepared in Example 4B is prepared at 350 to 1000 ppm of isothiazolone active ingredient. Freshly sawn timber is dipped in the solution for 30 seconds. The lumber is withdrawn from the solution and allowed to dry. The residual isothiazolone on the wood surface prevents staining due to fungal growth.

EXAMPLE 15

Use of Isothiazolone Microemulsion as a Laundry Mildewcide

A laboratory test was done using the microemulsion defined in Example 5C to determine its effectiveness as a laundry mildewcide. Pieces of fabric were washed in a commercial washing machine and treated with the composition of 5C diluted to the proper concentration in water. The fabric is exposed to the biocide for a 3 minute "rinse cycle". The fabric is air dried overnight then sprayed with Sabround Detrose Broth, a nitrogen source for the fungus (*A. niger*). After air drying the fabric is sprayed with a spore suspension of *A. Niger* in a 50 ppm solution of surfactant (octyl phenoxy polyethoxy (8) ethanol). Each piece of fabric is hung on a hook in a chamber in which the relative humidity is maintained at 94% and the temperature at 30° C. After 4 weeks storage the fabric is evaluated for percent fungal coverage.

Growth of *A. niger* on 100% cotton fabric treated with Isothiazolone Microemulsion 5C.

| Concentration of Active Ingredient in Fabric Treatment Solution[a] (ppm) | Percent Growth of A.Niger on 100% Cotton Fabric | |
| --- | --- | --- |
|  | Test 1 | Test 2 |
| 10 | 20 | 10 |
| 20 | 20 | 20 |
| 30 | 20 | 90 |
| 40 | NG[b] | T[c] |
| 50 | NG | NG |
| untreated control | 100 | 100 |

[a]Concentration of mildewcide based on the dry weight of fabric. Ratio of fabric treatment solution = 1.5.
[b]No Growth
[c]Trace of Growth This mildewcide treatment controlled the fungal growth at 40 ppm active ingredient or above.

What is claimed is

1. A microemulsion comprising from 0.1-50% by weight of an isothiazolone having a water solubility of less than 1% by weight of the formula:

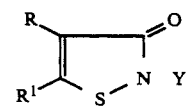

wherein Y is an unsubstituted alkyl group of 2 to 18 carbon atoms,
a substituted alkyl group of 2 to 18 carbon atoms having at least one hydrogen atom replaced by hydroxy, halo, cyano, alkylamino, dialkylamino, phenylamino, halophenylamino, carboxy, carbalkoxy, alkoxy, aryloxy, morpholino, piperidino, pyrrolidonyl, carbamoxy, or isothiazolonyl, wherein the total number of carbon atoms in the substituted alkyl group does not exceed 18,
an unsubstituted or halo-substituted alkenyl group of 4 to 18 carbon atoms,
unsubstituted or halo-substituted alkynyl group of 4 to 18 carbon atoms,
an unsubstituted or alkyl-substituted cycloalkyl group having a four to six carbon atom ring and up to 12 carbon atoms,
an unsubstituted or a halo-, lower alkyl-, or lower alkoxy-substituted aralkyl group wherein the total number of carbon atoms in the aralkyl group does not exceed 10; or
an unsubstituted or a halo-, nitro-, lower alkyl-, or lower carbalkoxy-, substituted aryl group wherein the total number of carbon atoms in the aryl group does not exceed 10; and
R and $R^1$ are the same or different substituent selected from hydrogen, halogen, or a ($C_1$–$C_4$) alkyl group; and
from 0.1 to 25% by weight of an anionic surfactant;
from 0.1 to 25% by weight of a cosurfactant selected from alkyl alcohols and alkylalkoxylated alcohols;
from 0.5 to 50% by weight of a polyoxyethylene/polyoxypropylene block copolymer of the formula:

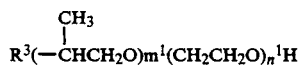

wherein $R^3$ is lower alkoxy or a radical of the formula $HO(CH_2CH_2O)_n{}^1$ where $m^1$ is an integer greater than 15 and $n^1$ is an integer greater than 10;
from 10 to 99% by weight of water; and from 0 to 30% by weight of an adjuvant or adjuvants.

2. The microemulsion of claim 1 comprising from 1 to 30% by weight of the isothiazolone; from 1 to 15% by weight of the anionic surfactant; from 1 to 20% by weight of the cosurfactant; from 1 to 40% by weight of the polyoxyethylene/polyoxypropylene copolymer; from 20 to 98% by weight of water and from 0 to 20% by weight of an adjuvant or adjuvants.

3. The microemulsion of claim 1 comprising from 1 to 12:5% by weight of the isothiazolone; from 1 to 4% of the anionic surfactant, from 1 to 6% of the cosurfactant; from 1 to 10% of the copolymer; from 50 to 90% water and from 0 to 16% of an adjuvant.

4. The microemulsion of claim 3 wherein the anionic surfactant is selected from alkylaryl sulfonate salts, alkyl ($C_8$–$C_{20}$) sulfate salts; $C_{10}$–$C_{20}$ fatty alcohol ethoxylate sulfate salts, mono- and dialkyl ($C_4$–$C_3$) sulfosuccinate salts, or sulfated oils.

5. The microemulsion of claim 3 wherein the cosurfactant is selected from $C_4$ to $C_{10}$ alkyl alcohols or alkylalkoxylated alcohols of the formula $CH_3(CH_2)_n(OC_2H_4)_mOH$ or $CH_3(CH_2)_n(OC_3H_6)_mOH$ wherein n is an integer of 0 to 7 and m is an integer of 1 to 4.

6. The microemulsion of claim 3 wherein the polyoxyethylene/polyoxypropylene copolymer has a molecular weight above 1750.

7. The microemulsion of claim 3 wherein the polyoxyethylene/polyoxypropylene copolymer has a molecular weight above 3000.

8. The microemulsion of claim 2 wherein the isothiazolone is n-octyl-4-isothiazolin-3-one.

9. The microemulsion of claim 6 wherein the isothiazolone is n-octyl-4,5-dichloroisothiazolone.

10. A method for preparing a microemulsion of a compound having a water solubility of less than 1% by weight of the formula:

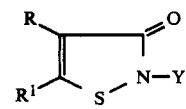

wherein Y is
an unsubstituted alkyl group of 2 to 18 carbon atoms,
a substituted alkyl group of 2 to 18 carbon atoms having at least one hydrogen atom replaced by hydroxy, halo, cyano, alkylamino, dialkylamino, phenylamino, halophenylamino, carboxy, carbalkoxy, alkoxy, aryloxy, morpholino, piperidino, pyrrolidonyl, carbamoxy, or isothiazolonyl, wherein the total number of carbon atoms in the substituted alkyl group does not exceed 18,
an unsubstituted or halo-substituted alkenyl group of 4 to 18 carbon atoms,
unsubstituted or halo-substituted alkynyl group of 4 to 18 carbon atoms,
an unsubstituted or alkyl-substituted cycloalkyl group having a four to six carbon atom ring and up to 12 carbon atoms,
an unsubstituted or a halo-, lower alkyl-, or lower alkoxy-substituted aralkyl group wherein the total number of carbon atoms in the aralkyl group does not exceed 10; or
an unsubstituted or a halo-, nitro-, lower alkyl-, or lower carbalkoxy-, substituted aryl group wherein the total number of carbon atoms in the aryl group does not exceed 10; and
R and $R^1$ are the same or different substituent selected from hydrogen, halogen, or a ($C_1$–$C_4$) alkyl group; and
which comprises mixing from 0.1 to 50% parts by weight of the compound with
from 0.1 to 25% an anionic surfactant;
from 0.1 to 25% a cosurfactant selected from alkyl alcohols or alkylalkoxylated alcohol;
from 0.5 to 50% by weight of a polyoxyethylene/polyoxypropylene block copolymer of the formula:

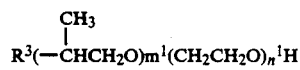

wherein $R^3$ is lower alkoxy or a radical of the formula $HO(CH_2CH_2O)_n{}^1$ where $m^1$ is an integer greater than 15 and $n^1$ is an integer greater than 10;
from 10 to 99% by weight of water; and from 0 to 30% by weight of an adjuvant or adjuvants.

11. The method of claim 10 which comprises mixing from 1 to 30% of the compound; from 1 to 15% of the anionic surfactant; from 1 to 20% of the cosurfactant; from 1 to 40% of the copolymer; from 20 to 98% of water; and from 0 to 20% of an adjuvant.

12. The method of claim 11 which comprises mixing from 1 to 12.5% of the compound, from 1 to 4% of the anionic surfactant; from 1 to 6% of the cosurfactant, from 1 to 10% of the copolymer; from 50 to 90% of water; and from 0 to 16% of an adjuvant.

13. The method of claim 12 wherein the anionic surfactant is selected from an alkylaryl sulfonate salts, alkyl ($C_8$–$C_{20}$) sulfate salts; $C_{10}$–$C_{20}$ fatty alcohol ethoxylate sulfate salts, mono- and dialkyl ($C_4$14 $C_{13}$) sulfosuccinate salts, or sulfated oils.

14. The method of claim 13 wherein the cosurfactant is selected from $C_4$ to $C_{10}$ alkyl alcohols or alkylalkoxylated alcohols of the formula: $CH_3(CH_2)_n(OC_2H_4)_mOH$ or $CH_3(CH_2)_n(OC_3H_6)_mOH$ wherein n is an integer of 0 to 7 and m is an integer of 1 to 4.

15. The method of claim 14 wherein the polyoxyethylene/polyoxypropylene copolymer has a molecular weight above 1750.

16. The method of claim 15 wherein the copolymer has a molecular weight above 3000.

17. The method of claim 16 wherein the compound is n-octyl-4-isothiazolin-3-one.

18. The method of claim 16 wherein the compound is n-octyl-4,5-dichloroisothiazolone.

19. A method for inhibiting the growth of bacteria, fungi, or algae in a locus subject to contamination by bacteria, fungi, or algae, which comprises incorporating onto or into the locus, in an amount which is effective to adversely affect the growth of bacteria, fungi, or algae, the microemulsion of claims 1, 2, 3, 4, 5, 6, 7, 8 or 9.

20. The method of claim 19 wherein the locus is an aqueous medium.

21. The method of claim 19 wherein the locus is a cutting oil formulation.

22. The method of claim 19 wherein the locus is a water-cooling system.

23. The method of claim 19 wherein the locus is a solid protective of decorative film.

24. The method of claim 19 wherein the locus is fabric, leather, paper, or wood.

25. The method of claim 19 wherein the locus is laundry wash water.

26. The method of claim 19 wherein the locus is a cosmetic formulation.

27. The method of claim 19 wherein the locus is a fuel system.

28. The method of claim 19 wherein the locus is plastic.

29. The method of claim 19 wherein the locus is an emulsion.

* * * * *